(12) United States Patent
Winslow et al.

(10) Patent No.: US 9,370,428 B2
(45) Date of Patent: *Jun. 21, 2016

(54) METHOD AND APPARATUS FOR PERFORMING A LESS INVASIVE SHOULDER PROCEDURE

(75) Inventors: Nathan A. Winslow, Warsaw, IN (US); Paul E. Schwartz, Palo Cedro, CA (US)

(73) Assignee: BIOMET MANUFACTURING, LLC, Warsaw, IN (US)

( * ) Notice: Subject to any disclaimer, the term of this patent is extended or adjusted under 35 U.S.C. 154(b) by 30 days.

This patent is subject to a terminal disclaimer.

(21) Appl. No.: 13/224,474

(22) Filed: Sep. 2, 2011

(65) Prior Publication Data

US 2011/0320004 A1  Dec. 29, 2011

Related U.S. Application Data

(63) Continuation of application No. 11/934,917, filed on Nov. 5, 2007, now Pat. No. 8,157,866.

(51) Int. Cl.
| | |
|---|---|
| *A61F 2/40* | (2006.01) |
| *A61B 17/16* | (2006.01) |
| *A61F 2/30* | (2006.01) |
| *A61B 17/17* | (2006.01) |

(52) U.S. Cl.
CPC ........... *A61F 2/4014* (2013.01); *A61B 17/1684* (2013.01); *A61B 2017/1778* (2013.01); *A61F 2/4081* (2013.01); *A61F 2002/30332* (2013.01); *A61F 2002/30339* (2013.01); *A61F 2002/30341* (2013.01); *A61F 2002/30344* (2013.01); *A61F 2002/30604* (2013.01); *A61F 2002/30616* (2013.01); *A61F 2002/4022* (2013.01); *A61F 2002/4051* (2013.01); *A61F 2002/4062* (2013.01); *A61F 2002/4085* (2013.01); *A61F 2220/0033* (2013.01)

(58) Field of Classification Search
CPC . A61F 2/4014; A61F 2/32; A61F 2002/4635; A61F 2/40; A61B 17/1684
USPC .......................................... 623/19.11–19.14
See application file for complete search history.

(56) References Cited

U.S. PATENT DOCUMENTS

| | | |
|---|---|---|
| 3,979,778 A | 9/1976 | Stroot |
| 4,206,517 A | 6/1980 | Pappas et al. |
| 5,282,865 A | 2/1994 | Dong |

(Continued)

OTHER PUBLICATIONS

Delta CTA™ Reverse Shoulder Prosthesis Surgical Technique, DePuy International Ltd.*

(Continued)

*Primary Examiner* — Corrine McDermott
*Assistant Examiner* — Joshua Levine
(74) *Attorney, Agent, or Firm* — Schwegman Lundberg & Woessner, P.A.

(57) ABSTRACT

A method for performing an arthroplasty on at least one of a glenoid or a humerus of a glenohumeral joint. The method includes the following: forming an entry incision in soft tissue superior and lateral to the glenohumeral joint; forming a passage from the entry incision to the glenohumeral joint; inserting a cutting instrument through the passage and cutting a humeral head of the humerus to prepare the humerus to receive an implant including a stem; inserting the implant through the passage; and securing the implant relative to the humerus with the implant oriented such that the stem extends substantially parallel to a longitudinal axis of the humerus.

17 Claims, 12 Drawing Sheets

(56) References Cited

U.S. PATENT DOCUMENTS

| | | | |
|---|---|---|---|
| 5,358,526 A | 10/1994 | Tornier | |
| 5,489,309 A | 2/1996 | Lackey et al. | |
| 5,702,486 A | 12/1997 | Craig et al. | |
| 5,910,171 A | 6/1999 | Kummer et al. | |
| 6,168,628 B1 * | 1/2001 | Huebner | 623/19.11 |
| 6,193,758 B1 | 2/2001 | Huebner | |
| 6,197,062 B1 | 3/2001 | Fenlin | |
| 6,368,352 B1 | 4/2002 | Camino et al. | |
| 6,494,913 B1 | 12/2002 | Huebner | |
| 6,514,287 B2 | 2/2003 | Ondrla et al. | |
| 6,589,282 B2 | 7/2003 | Pearl | |
| 6,719,799 B1 | 4/2004 | Kropf et al. | |
| 6,863,690 B2 | 3/2005 | Ball et al. | |
| 6,942,699 B2 | 9/2005 | Stone et al. | |
| 2005/0043805 A1 * | 2/2005 | Chudik | 623/19.14 |
| 2005/0119531 A1 * | 6/2005 | Sharratt | A61B 17/02 600/227 |
| 2011/0112648 A1 * | 5/2011 | Gunther | 623/19.11 |

OTHER PUBLICATIONS

Copeland, S. et al., Surface Replacement Arthroplasty of the Shoulder, pp. 1-19 (Undated).

Copeland, Stephen A. et al., Resurfacing Arthroplasty of the Shoulder, Techniques in Shoulder & Elbow Surgery 4(4): pp. 199-210, Lippincott Williams & Wilkins, Inc, Philadelphia (2003.

Levy, O. et al., Cementless Surface Replacement Arthroplasty of the Shoulder, 5- to 10-Year Results with the Copeland Mark-2 Prosthesis, The Journal of Bone & Joint Surgery (Br), vol. 83-B, No. 2, Mar. 2001, pp. 213-221.

Copeland, S., Cementless Total Shoulder Replacement, Royal Berkshire Hospital, Berkshire, United Kingdom, pp. 289-293 (Undated).

Biomet Orthopedics, Copeland/Copeland EAS Humeral Resurfacing Head, Surgical Technique, pp. 1-24 (2008).

* cited by examiner

FIG. 22

METHOD AND APPARATUS FOR PERFORMING A LESS INVASIVE SHOULDER PROCEDURE

CROSS-REFERENCE TO RELATED APPLICATION

This application is a continuation of U.S. patent application Ser. No. 11/934,917 filed on Nov. 5, 2007, the disclosure of which is incorporated herein by reference.

FIELD

The present disclosure relates to a method and apparatus for performing a less invasive shoulder procedure.

BACKGROUND

This section provides background information related to the present disclosure which is not necessarily prior art.

An anatomy, such as a human anatomy, includes various articulations, soft tissues, and hard tissues to perform various functions. Generally, these functions are carried out pain-free and with a substantial range of motion. Nevertheless, various functions may deteriorate over time as soft tissue or hard tissue deteriorates and articulations deteriorate. At a selected time, various portions of the anatomy may be replaced with artificial portions to restore substantially normal or anatomical motion and functionality.

For example, the articulation of the humerus with the glenoid (the glenohumeral or shoulder joint) may deteriorate. The humeral head or the glenoid may deteriorate and become rough or lose their anatomical shapes and reduce motion, increase pain, or the like. This may happen for various reasons, such as injury, disease, or lack of motion. This may lead to replacement of the selected portions of the anatomy with a prosthesis to achieve a substantially normal or anatomical range of motion.

Although it is known to replace various portions of the anatomy, such as a humeral head and a glenoid, many procedures generally require large incisions through soft tissue. Further, various procedures require that many muscle and muscle attachments be cut to achieve access to selected portions of the anatomy. Although it may be selected or necessary to perform many procedures in this manner, it may also be desirable to achieve a less invasive procedure.

Further areas of applicability of the present teachings will become apparent from the description provided hereinafter. It should be understood that the description and various examples, while indicating various embodiments, are intended for purposes of illustration only and are not intended to limit the scope of the teachings.

SUMMARY

This section provides a general summary of the disclosure, and is not a comprehensive disclosure of its full scope or all of its features.

The present teachings provide for a method for performing an arthroplasty on at least one of a glenoid or a humerus of a glenohumeral joint. The method includes the following: forming an entry incision in soft tissue superior and lateral to the glenohumeral joint; forming a passage from the entry incision to the glenohumeral joint; inserting a cutting instrument through the passage and cutting a humeral head of the humerus to prepare the humerus to receive an implant including a stem; inserting the implant through the passage; and securing the implant relative to the humerus with the implant oriented such that the stem extends substantially parallel to a longitudinal axis of the humerus.

The present teachings further provide for a method for performing an arthroplasty on at least one of a glenoid or a humerus of a glenohumeral joint. The method includes the following: forming an entry incision in soft tissue superior and lateral to the glenohumeral joint; forming a passage from the entry incision to the glenohumeral joint through a deltoid muscle substantially superior and lateral of the glenohumeral joint; inserting a cutting instrument through the passage and cutting a humeral head of the humerus while the humeral head is in cooperation with a glenoid to prepare the humerus to receive an implant; inserting through the passage the implant including an articulation surface with a first axis extending through an axial center of the articulation surface, a planar coupling surface that extends in a plane orthogonal to the first axis, and a stem with a second axis extending through an axial center of the stem, the second axis is non-orthogonal to the coupling surface; orienting the implant such that the second axis is substantially parallel to a longitudinal axis of an intramedullary canal of the humerus; and securing the implant relative to the humerus.

The present teachings also provide for a method for performing an arthroplasty on at least one of a glenoid or a humerus of a glenohumeral joint. The method includes forming an entry incision in soft tissue superior and lateral to the glenohumeral joint; forming a passage from the entry incision to the glenohumeral joint through a deltoid muscle substantially superior and lateral of the glenohumeral joint; inserting a cutting instrument through the passage and cutting a humeral head of the humerus while the humeral head is in cooperation with a glenoid to prepare the humeral head to receive an implant including an articulation surface and a stem; resecting at least a portion of the humeral head while the humeral head is in cooperation with the glenoid; inserting the implant through the passage, and securing the implant relative to the humerus with the implant oriented such that the stem is confined to an area superior to an intramedullary canal of the humerus and extends substantially parallel to a longitudinal axis of the humerus; and maintaining a subscapularis muscle and a supraspinatus muscle proximate to the glenohumeral joint intact and completely connected to surrounding bone during the entire arthroplasty procedure.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
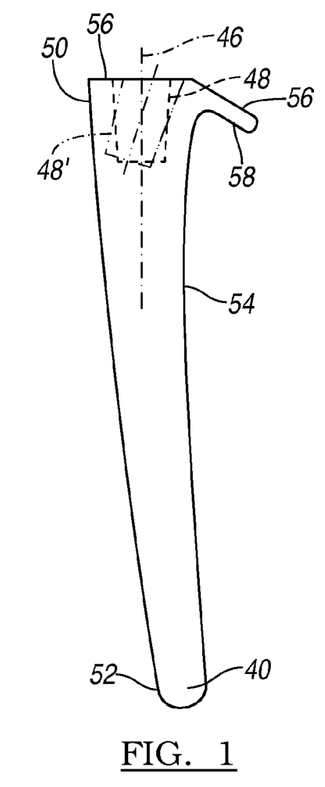
FIGS. 1-3 represent alternate prosthetic stems according to the teachings of the present invention.
Figure 2:
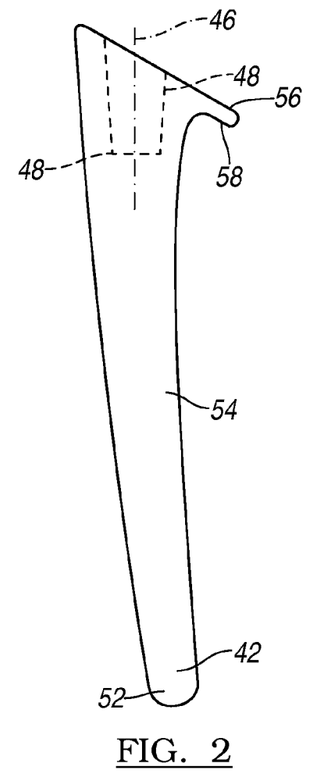
Figure 3:
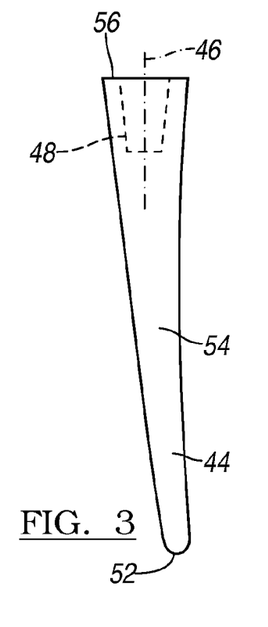

FIGS. 1-3 represent alternate stem prosthetics according to the teachings of the present invention. Stems 40, 42 and 44 have a defined central stem axis 46, which as described below generally corresponds to the central axis of a humeral medullary canal. The stem 40 has a locking mechanism 48 shown as a female locking taper formed on a stem proximal end 50. Additionally defined on the stem proximal end 50 is an optional head support surface 56 and a humeral engaging surface 58. The locking mechanism 48 is generally parallel to and can be co-axial with the central stem axis 46.

The stems 40, 42 and 44 are configured to be implanted into a humeral medullary canal prior to the coupling of the stem 40 to a humeral head 60. The stem 40 is implanted into the canal by applying impact forces along the central stem axis 46. This direction is independent of the angle of the head support surface 56. As described below, the stem 40 is configured to accept the humeral head 60 after the stem 40 has been implanted into the patient. This allows a significant reduction in the size of the needed incision in the subscapularis muscle.

Figure 4:
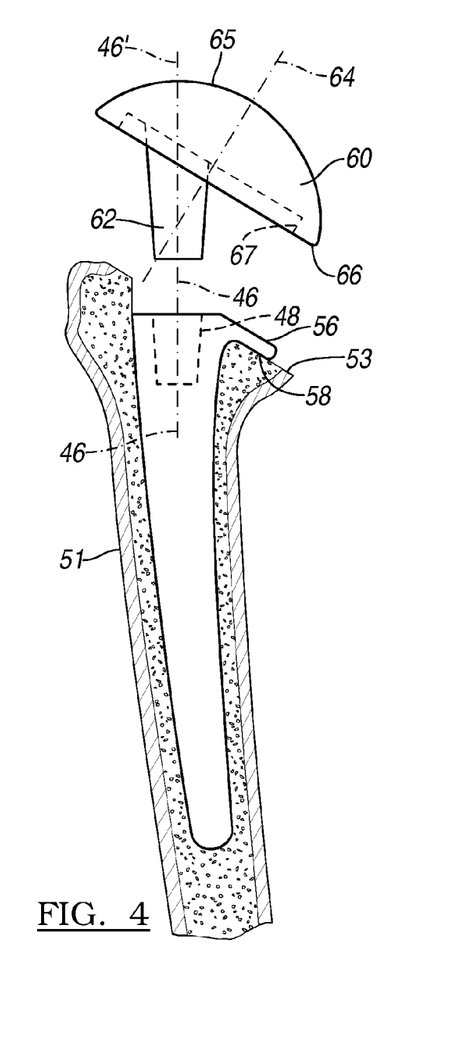
FIGS. 4 and 5 represent the implantation of the stem shown in FIG. 1 into a resected humerus.
Figure 5:
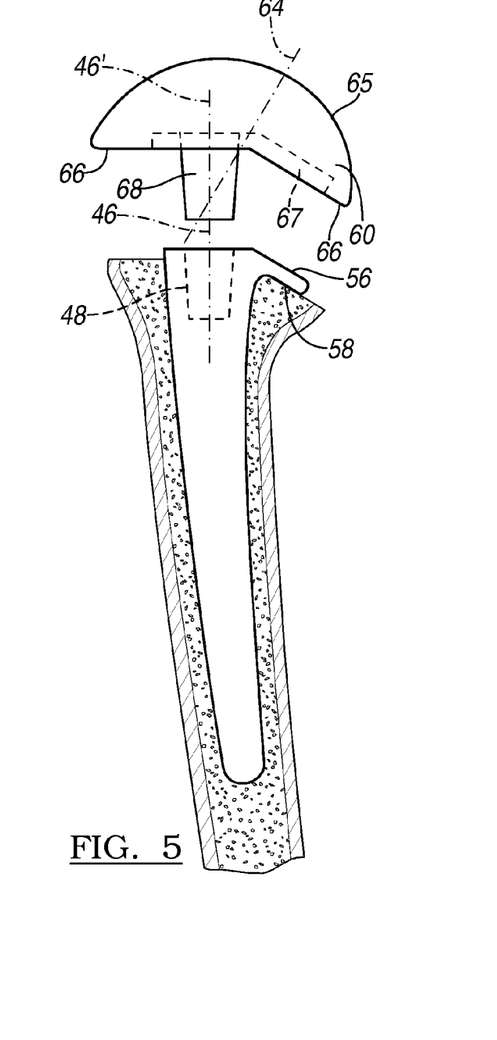

As shown in FIGS. 4-7, the prosthetic has humeral head 60 with a coupling mechanism 62. The coupling mechanism 62 can be a male locking taper configured to couple with the locking mechanism 48 within the stem proximal end 50 of the stems 40, 42 and 44. The coupling mechanism 62 has a central stem axis 46', while a head central axis 64 defines a head articulating surface 65. The humeral head 60 has a stem bearing surface 66 opposite the head articulating surface 65, and an optional recess area 67. The stem bearing surface 66 can be generally flat or can be multi-surfaced as is shown in FIG. 5.

The central stem axis 46' is angularly offset from the head central axis 64. The stem can be offset between 0 and 55 degrees. Optionally, the central stem axis 46' is generally not perpendicular to the stem bearing surface 66. In the multi-surfaced bearing shown in FIG. 5, it is envisioned one of the bearing surfaces can be generally perpendicular to the central stem axis 46'. The central stem axis 46' is intended to be aligned with the central stem axis 46.

Figure 6:
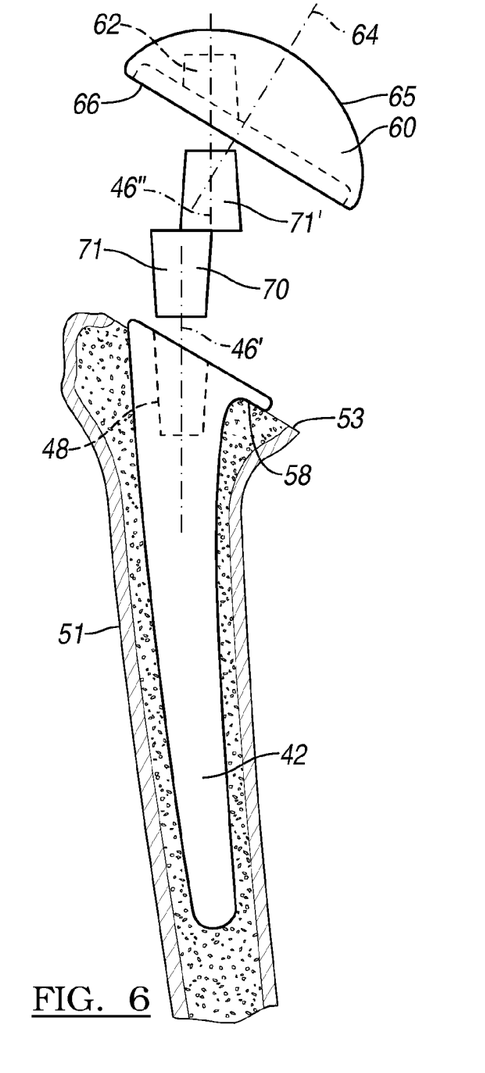
FIGS. 6 and 7 represent cross sections of a resected humerus with implanted stems according to FIGS. 2 and 3 with associated alternate prosthetic coupling mechanisms.
Figure 7:
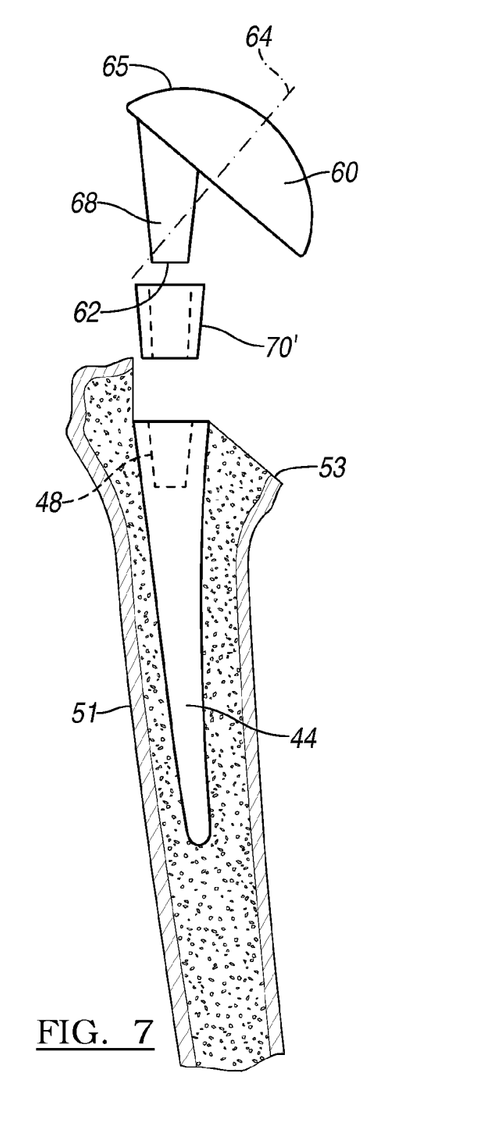

As shown in FIGS. 6 and 7, the humeral head 60 can be coupled to the stems 40, 42, 44, using an intermediate coupling member 70 and a superior surgical approach. The intermediate coupling member 70 can be formed of a pair of male locking tapers 71 and 71'. These male locking tapers 71 and 71' define central stem axes 46' and 46", which are offset to the central stem axis 46. The offset axes function to allow a physician to adjust the positions of the humeral head 60 with respect to the central stem axis 46 to improve mobility of the joint. The humeral head 60 can be positioned less than about 2 mm from the stem 40, and assembled insitu.

Figure 12:
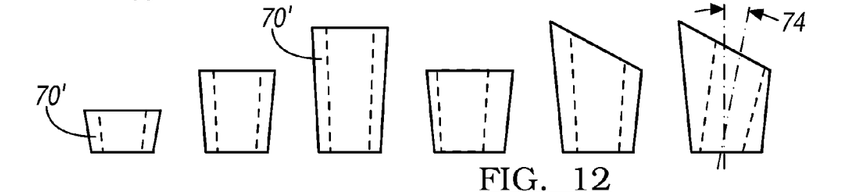
FIG. 12 represents a set of humeral head offsets.

As shown in FIGS. 7 and 12, the intermediate coupling member 70 can take the form of an annular member 70'. The annular member 70' defines internal and external locking taper surfaces. These surfaces are configured to couple to the locking mechanism 48 in the stem proximal end 50, and coupling stem 68 of the humeral head 60. Optionally, the internal locking taper can angularly or transversely adjust the position of the humeral head 60.

Figure 8:
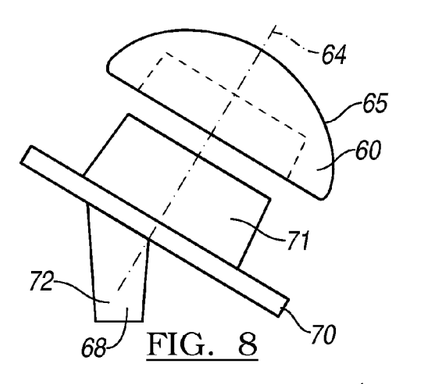
FIGS. 8-11 represent alternate humeral head fixation adaptors.
Figure 9:
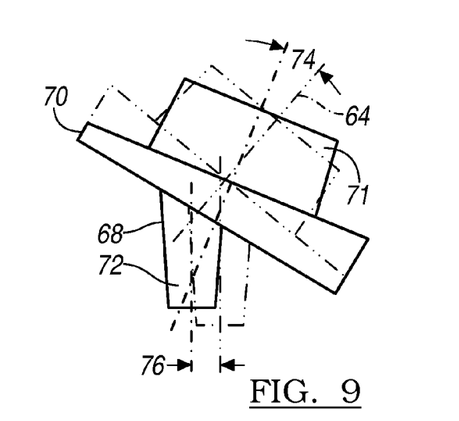
Figure 10:
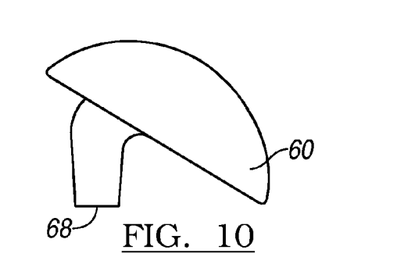
Figure 11:
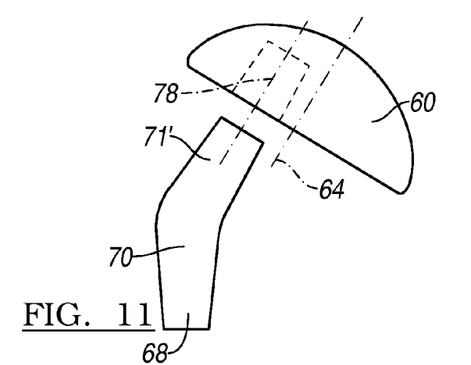

FIGS. 8-13 represent coupling members that are configured to couple the humeral head 60 to the stem proximal end 50. As shown in FIGS. 8 and 9, the intermediate coupling members 70 can have coupling stems 68 that are configured to be parallel to the central stem axis 46 of the stem 40. Additionally, the coupling mechanisms can have a male locking taper 71 which is parallel to the head central axis 64. As shown in FIG. 9, the axis of the male locking taper 71 can be at an angle 74 relative to the head central axis 64 so as to adjust the angular displacement of the humeral head 60 with respect to the central stem axis 46.

Figure 13:
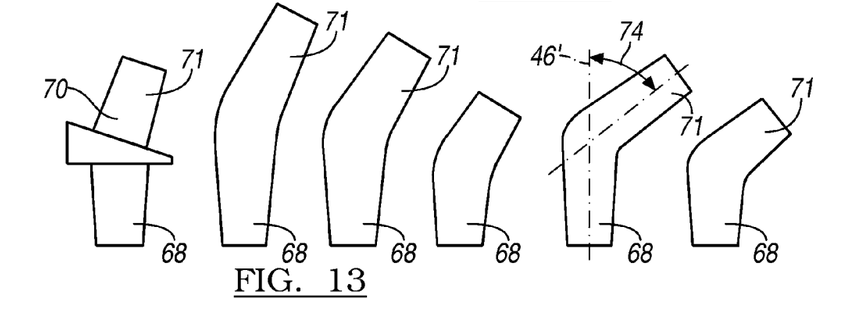
FIG. 13 represents a set of angled humeral head fixation members.

FIGS. 12 and 13 represent a kit of intermediate coupling members 70 and annular members 70'. As additionally shown in FIG. 7, the annular members 70' can be used to change the displacement of the humeral head 60 from the head support surface 56. FIG. 13 represents a kit of intermediate coupling members 70 each having a pair of coupling tapers. The tapers are of varying lengths and angles 74. The intermediate coupling members 70 can be coupled to the humeral head 60 prior to the coupling of the humeral head 60 to the stem 40.

Figure 14A:
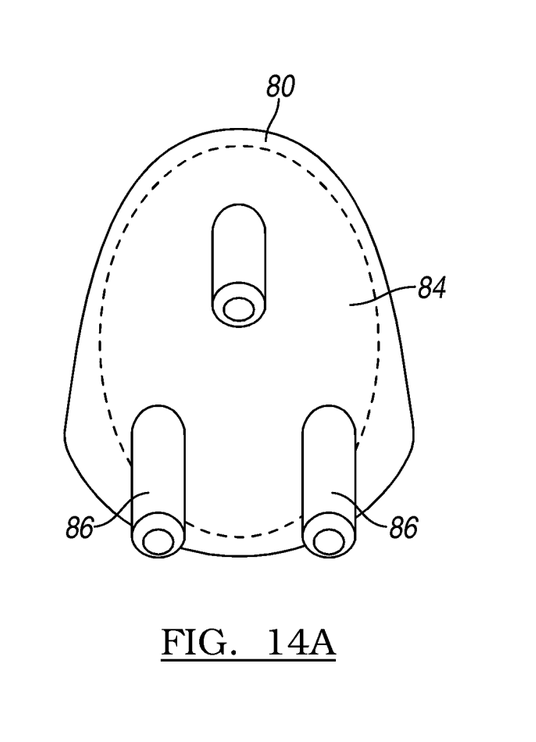
FIGS. 14a and 14b represent a glenoid according to one embodiment.
Figure 14B:
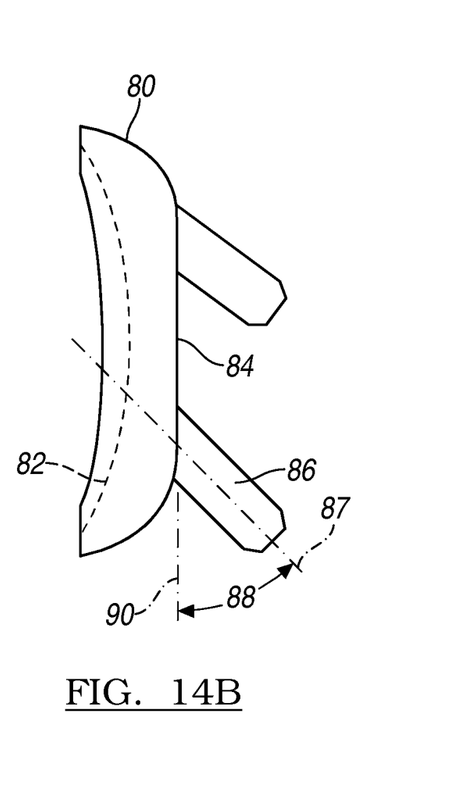

FIGS. 14a and 14b represent rear and side views of a glenoid prosthetic 80 configured to be used in a joint arthroplasty as described below. The glenoid prosthetic 80 has a curved bearing surface 82 and generally flat bearing surface 84. The generally flat bearing surface 84 is configured to be coupled to a resected glenoid and has a plurality of coupling pegs 86. The coupling pegs 86 have a plurality of axes 87 which are a predetermined angle 88 from plane 90 which defines the generally flat bearing surface 84. The predetermined angle 88 can be between about 100 to about 60 degrees, and preferably between about 30 to about 45 degrees. The glenoid prosthetic 80 and coupling pegs 86 are configured to allow the insertion of the glenoid prosthetic 80 using a superior approach through an incision to the resected glenoid.

Figure 15:
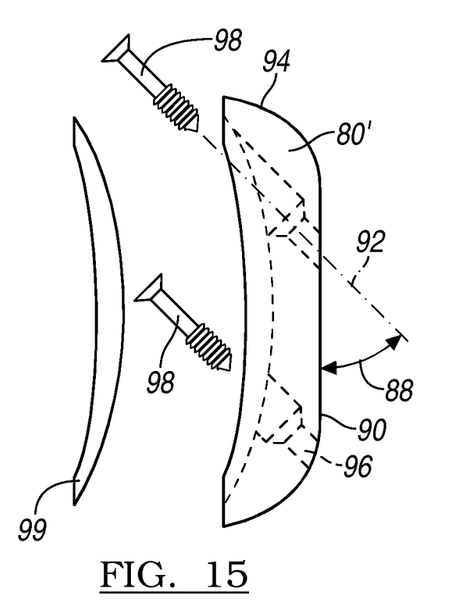
FIG. 15 represents an alternate glenoid.

As shown in FIG. 15, the glenoid prosthetic 80' can take the form of a metallic base 94 and a polymer bearing member 99. The metallic base 94 is coupled to the resected glenoid using bone coupling screws 98. The bone coupling screws 98 are configured to be driven through a plurality of bone screw accepting apertures 96. The apertures 96 are angled in a manner which allows for access through the superior approach.

Various instruments can be used in performing a selected procedure, such as a shoulder arthoplasty. It will be understood that various instruments and procedures may be used to perform a hemi-arthoplasty, such as replacement of only one of a humeral head or a glenoid. A total arthoplasty can be the replacement of a humeral head and a glenoid where the humeral head and the glenoid can articulate with one another after implantation.

Described below and illustrated in FIGS. 16a-19 is a procedure performed relative to a human anatomy 300. It will be understood that the following method is merely exemplary and is not intended to limit the scope of the above-described instruments. Similarly, the procedure herein is exemplary of a procedure that may be performed relative to a selected portion of the anatomy and, although a shoulder procedure is described, it is not intended to limit the teachings herein.

Figure 16:
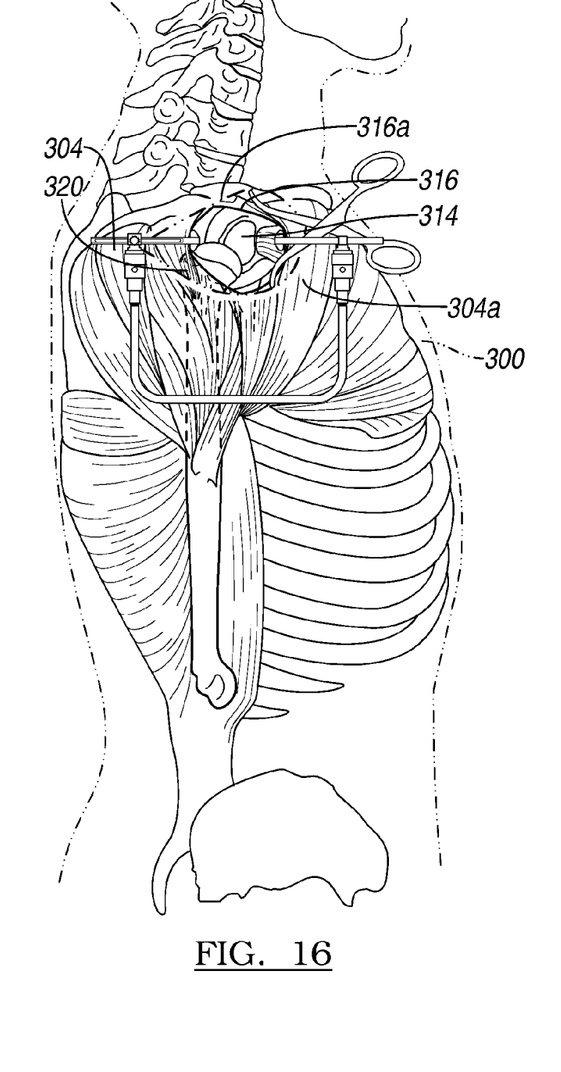
FIGS. 16-19 depict the preparation of the human anatomy to accept the implants of FIGS. 1-15.
Figure 20A:
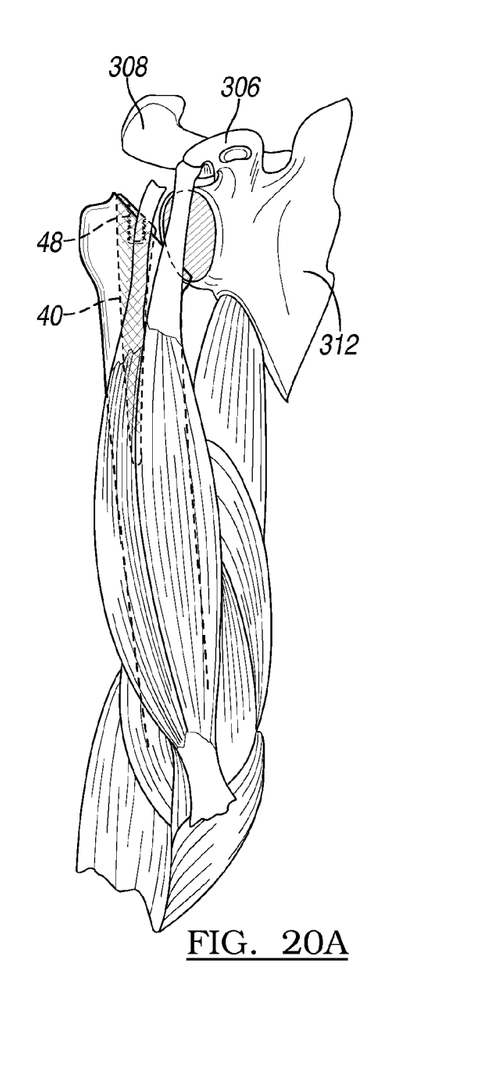
FIGS. 20a and 20b represent the implantation of the stem shown in FIG. 1 and the glenoid of FIG. 14.

With initial reference to FIGS. 16 and 20a, human anatomy 300 can be augmented with the use of the instruments. The human anatomy 300 generally includes an external skin layer and soft tissue there below, such as muscle 304. Various portions of the anatomy, including natural humerus 310 and natural glenoid 314, can be accessed by forming an incision 316 in the soft tissue, including the skin.

Also, various subdermal portions, such as subdermal adipose tissue, can be incised along the incision 316. It will be understood that the incision 316 can be orientated in any appropriate direction such as anterior to posterior, which is generally parallel to a sagittal plane. In this regard, the incision is about 5 cm in length. Alternatively, or in addition thereto, a superior-inferior incision 316a illustrated in phantom, which is generally along the coronal plane, can be made. The skin incision can made parallel with Langerhan's lines at the superior aspect of the shoulder, just even with the lateral border of acromion 306. The incision 316 can also be medialized slightly. The incision 316 can be any appropriate length, and may depend upon surgeon preference, patient type, prosthetics to be used, or other indications. Nevertheless the incision can be about 3 cm (about 1 in) to about 20 cm (8 in) in length such as about 7.5 cm (about 3 in) to about 10 cm (4 in). It will be understood that the incision 316 through the skin may be shorter than the area opened in the muscle 304. The incision 316 can be used to achieve access to the muscle 304 that is around the various portions of the anatomy that are selected to be resected, including the natural humerus 310 and the natural glenoid 314. The incision can be used to obtain access to a deltoid muscle 304a.

The retractor can be any appropriate retractor such as a Gelpi Style Retractor. It will be understood that the retractor may also be used to retract the soft tissue, such as the muscles surrounding the glenohumeral joint, including the deltoid muscle 304a, but the Gelpi Style Retractor may also be used to expand the incision 316 to gain access to the muscle. The retractor can be used to retract or position the deep tissue that is generally near the glenohumeral joints.

The passage 320 through the deltoid muscle 304a can achieve access to various deeper soft tissue portions, such as the sub-deltoid bursa and the subacromial bursa without damaging the rotator cuff. Further, various other deep soft tissue can be incised and/or moved to achieve access to the capsule surrounding the shoulder or glenohumeral joint. After moving and/or incising all of these portions, access to the natural humerus 310 or the natural humeral head 310a can be achieved.

The retractor can be used to hold the various soft tissues portions open, such as the cuff interval, capsule and the like. It will be understood that the retractor may be any appropriate retractor and may include a scissor retractor or the like. Various other soft tissue portions may be near the capsule and may also be incised or resected. For example, the bicep tendon that interconnects to a portion or near the natural humeral head 310a may be resected or may be moved, if already detached, to achieve better access to the natural humeral head 310a. Further, access to the natural glenoid 314 can also be seen once the soft tissue has been incised.

Although the incision 316 on the shoulder or near the glenohumeral joint allows access to the deltoid muscle 304a and access to the capsule and soft tissue surrounding the glenohumeral joints, various muscles and ligaments need not be resected or incised when obtaining access to the glenohumeral joint according to the process discussed herein. For example, the subscapularis muscle and the ligaments attaching it to the portions of the glenohumeral joint need not be incised when obtaining access to the glenohumeral joint according to embodiments of the teachings herein. The subscapularis muscle can be left intact because it is generally anterior from the approach described. Also the supraspinatus can remain intact, as may all the muscles of the rotator cuff. Rather the passage 320 can be formed by separating the cuff interval rather than detaching or incising various soft tissue portions. Further, the natural humeral head 310a need not be substantially dislocated or dislocated at all from the glenohumeral joint according to various embodiments. Rather, the natural humeral head 310a can be moved to allow access to various portions of the anatomy, however, major dislocation of the natural humeral head 310a from the natural glenoid 314 is not necessary. The humerus can be left in its generally anatomical position or retracted any appropriate distance, such as about 2 cm to about 8 cm.

The soft tissue over the biceps laterally is sharply dissected off the humerus down to the top of the subscapularis tendon, but the tendon can be left undisturbed. The supraspinatus may be stripped back off the anterior portion of the greater tuberosity for a distance of about 5 mm to about 10 mm to further enhance the exposure. More than about 1 cm may not be detached, and the basic integrity of the tendon can remain. This exposure of the rotator interval typically gives about a 1.5 cm to about 2 cm gap at the lateral edge, without disrupting the rotator cuff mechanism. The Gelpi retractor can be moved from the deltoid muscle 304a to the rotator interval and this can provide greater exposure of the glenohumeral joint for instrumentation and implants.

Figure 17:
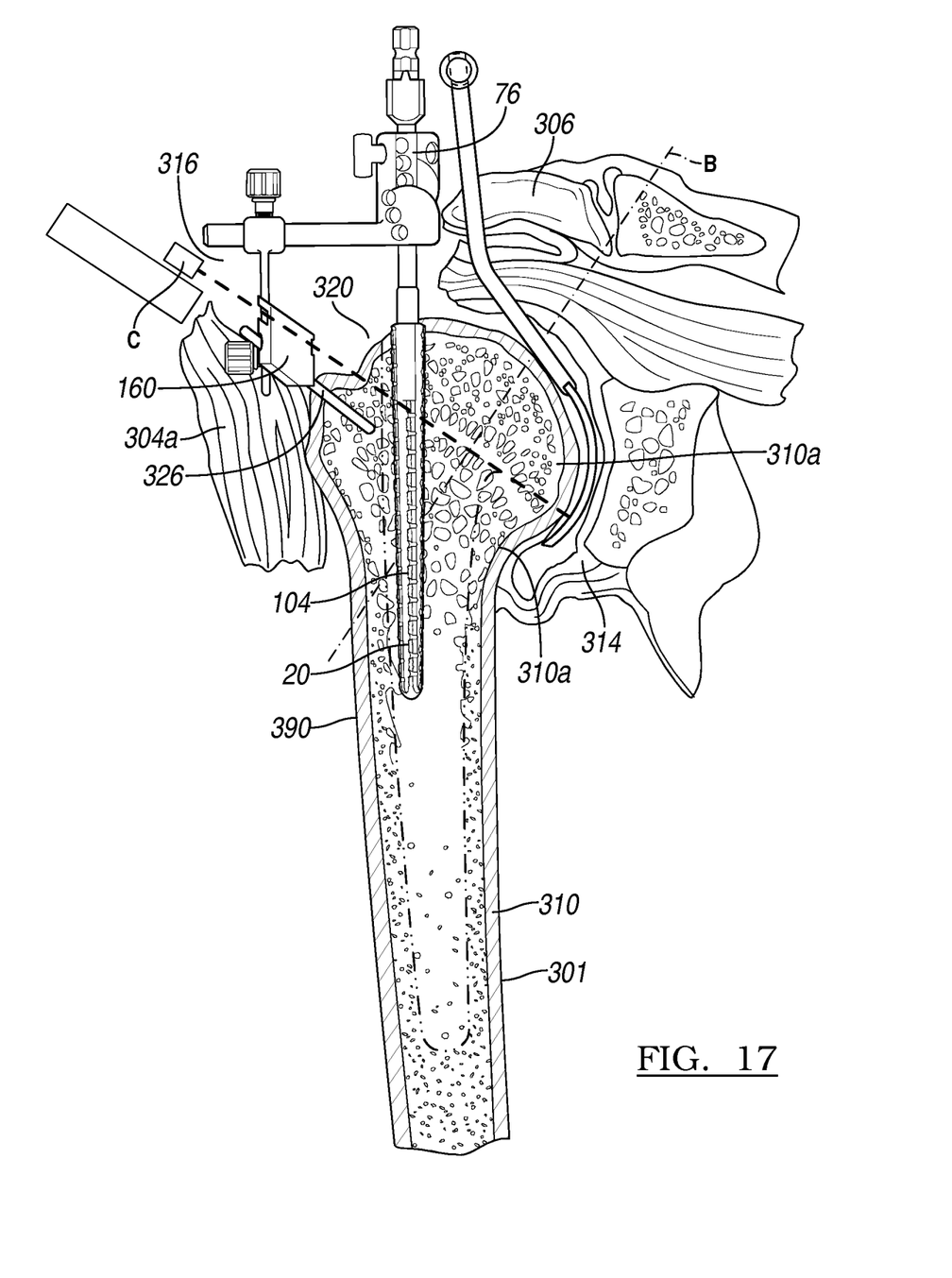

Once access has been obtained to the glenohumeral joint, various instruments according to various embodiments can be used in the procedure. It will be understood that according to various embodiments, any, all, or none of the instruments may be used in a procedure. With reference to FIG. 17 (detailed view of the glenohumeral joint), reamer 20 can be reamed into the natural humerus 310 near the natural humeral head 310a. Humeral reaming can occur from the superior, lateral humeral head. The entrance to the natural humeral head 310a can be just underneath the previous location (i.e. the natural location) of the biceps tendon. The arm 301 can be extended slightly, and the elbow can be placed against the patient's side to bring the top of the natural humeral head 310a forward, and allow the reamer to pass the front of the acromion 306. This can allow the natural humeral head 310a to be retracted, but remain substantially or completely undislocated. This can reduce trauma in the surrounding soft tissue. The superior approach allows easy centering of the reamer in the humeral head and proximal shaft, and decrease the initial incidence of varus stem placement and/or eccentric head utilization.

The reamer 20 includes a shaft 104 that can extend from the natural humerus 310. The reamer 20 can be positioned into the humerus and interconnected with various portions, such as guide apparatus 76. The guide apparatus 76 can be interconnected with the shaft 104 of the reamer 20 while the reamer remains in the natural humerus 310. This allows for positioning a cutting guide 160 relative to the natural humerus 310 and the natural humeral head 310a.

The various portions of the guide apparatus 76, including the guide movement arm, can be used to orient the cutting guide 160 in a proper orientation relative to the natural humeral head 310a. Generally, it is selected to obtain or position an axis of the cutting guide 160, such as a central axis, relatively in line with the natural humerus 310. This can help position the guide surface generally perpendicular to an axis B of the natural humeral head 310a. The axis B is generally about perpendicular to a plane or line C that extends through the natural humeral head 310a occurs on this plane or line C.

The cutting guide 160 can generally be positioned at about 20 degrees to about 30 degrees of retroversion. Once the cutting guide 160 is positioned in a selected position, it may be held in place with a fixation pin 326. It will be understood that more than one fixation pin 326 can be provided and pass through bores 186, defined by the cutting guide 160. The pins can include any appropriate type of pin and can be drilled into the natural humerus 310 to hold the cutting guide 160 relative thereto. The various other portions of the guide apparatus, including fixation arm 170 and guiding arm 172, can then be removed from the reamer 20. In addition, the reamer 20 can be removed from the humerus to allow for a resection of the natural humeral head 310a.

The cutting guide 160 can be held in place with the fixation pin 326 when all the other portions of the apparatus are removed. The saw can then be used to resect the humeral head and the blade can ride along a portion of the cutting guide 160. The cutting guide 160 can insure a proper orientation and/or position of the saw blade relative to the natural humeral head 310a. Further, a glenoid shield can be positioned relative to the natural glenoid 314 and other portions of the anatomy to assist in ensuring that saw 200 does not engage portions of the anatomy not desired to be cut.

It will be also understood that the cut of the natural humeral head 310a can be begun with the cutting guide 160 and then finished without the cutting guide 160. For example, an initial portion of the natural humeral head 310a can be resected with use of the cutting guide 160. After an initial portion of the cut is formed, the cutting guide 160 and the fixation pins 326 can be removed. The remainder of the cut of the natural humeral head 310a can then be performed using the initial portion of the cut formed with the saw blade to guide the remaining portion of the cut. Therefore, it will be understood, that the cutting guide 160 need not be present to form the entire cut of the natural humeral head 310a.

The glenoid condition can also be assessed, and a decision can be made for hemiarthroplasty or total shoulder arthroplasty. The glenoid is well visualized, and directly approached, as the surgical exposure is lateral as compared to other techniques. Glenoid version, glenoid erosions, and glenoid osteophytes are all easily assessed. Labral tissue is cleared from around the margins, and glenoid preparation can be carried out with a selection of straight reamers and drills. As described below, a keeled or pegged glenoid implant can be utilized, per the surgeon's preference as discussed herein. Although the procedure can proceed according to any appropriate technique, glenoid preparation and implantation can occur prior to humeral broaching, but the humerus could be prepared first if desired.

Figure 18:
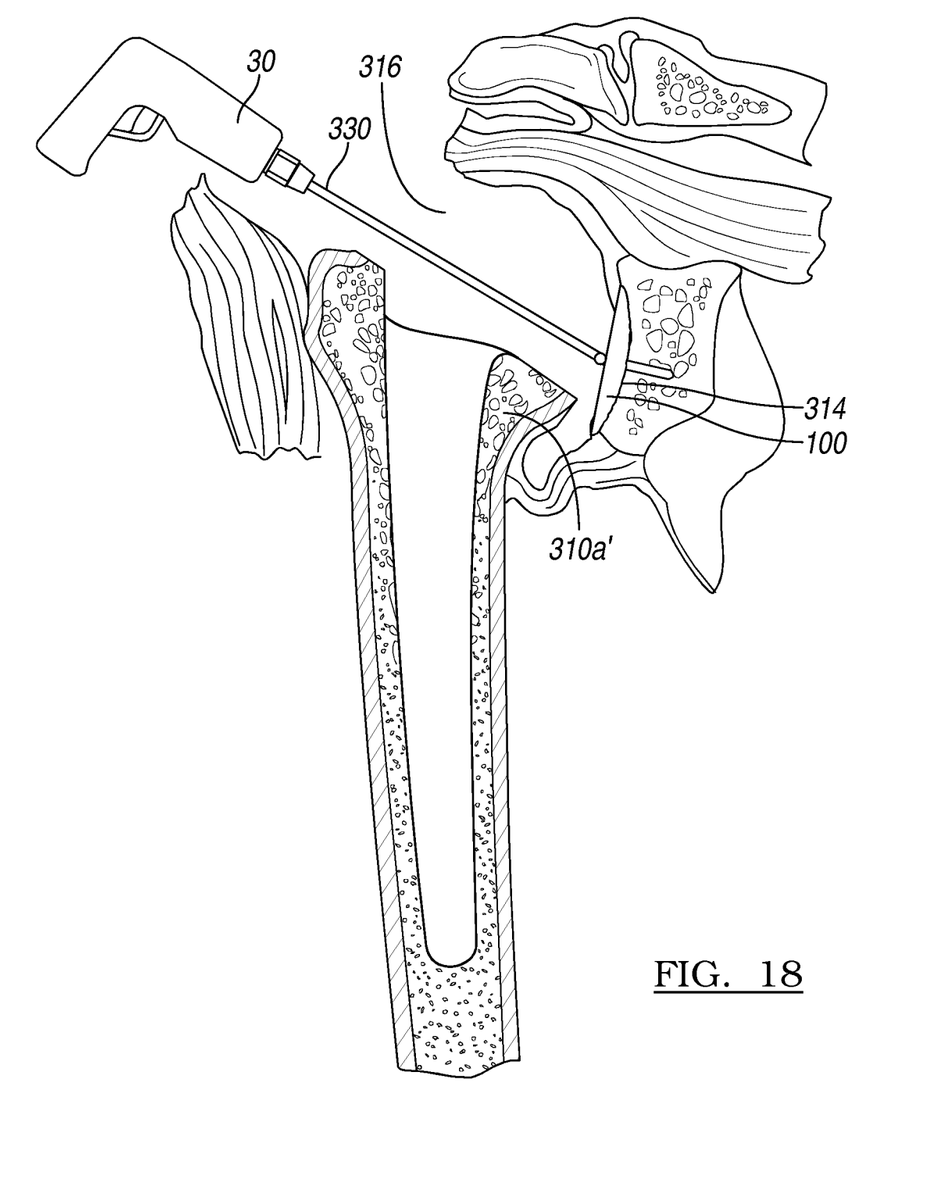

With reference to FIG. 18, once the natural humeral head 310a has been resected, thus forming the resected natural humeral head 310a', the natural glenoid 314 can be reamed with reamer 100. It will be understood that the natural glenoid 314 may be first prepared with the various procedures according to those commonly known in the art. Nevertheless, it will be understood that the various guides, such as those described herein, can be used to assist in achieving these procedures. As discussed above, various connecting portions can be positioned at a superior or top portion of the sizer or other instrument to assist in achieving the superior approach described herein. The reamer 100 can be interconnected with a reamer shaft 330 and a drill motor 30. This allows the reamer 100 to be rotated relative to the natural glenoid 314 to form the glenoid into a selected shape and orientation. The natural glenoid 314 may need to be shaped to allow for implantation of a selected glenoid implant. Nevertheless, it will be understood that the natural glenoid 314 need not necessarily be resected and may articulate with an implant positioned in the resected natural humerus 310.

Regardless, the reamer 100 can be positioned relative to the natural glenoid 314 and the shaft 313 extend through the incision 316 to allow for interconnection with the drill motor 30. After a selected period of reaming, the natural glenoid 314 can be prepared for implantation of a glenoid implant. As discussed above, the glenoid prosthetic 80 can be positioned relative to the reamed natural glenoid 314a to assist in further glenoid preparation.

Figure 19:
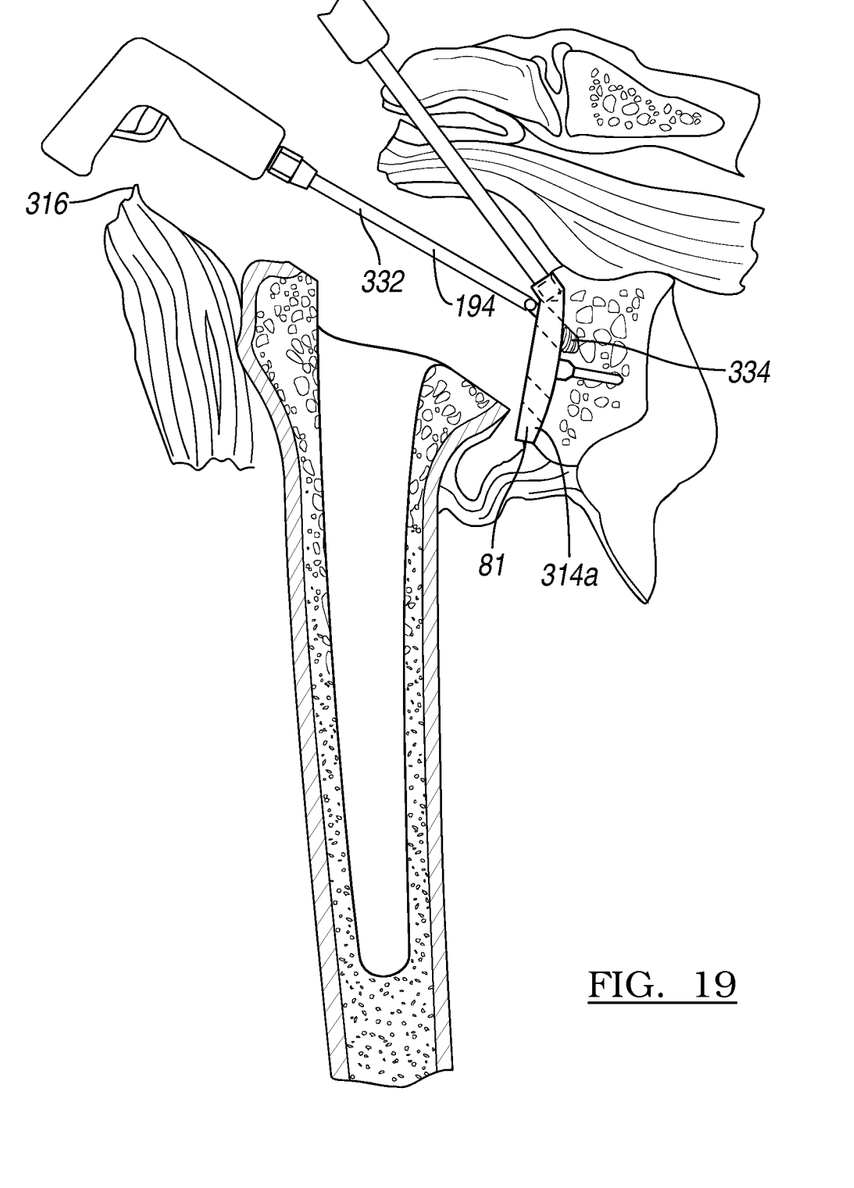

With reference to FIG. 19, a glenoid template 81 can be positioned relative to the reamed natural glenoid 314a. The glenoid template 81 allows for drilling or forming a plurality of bores in the reamed natural glenoid 314a with a bit 334 that can be interconnected to the drill motor 30 with a shaft 332. The various bores formed in the reamed natural glenoid 314a allow for interconnection and positioning of portions of a glenoid implant, such as pegs extending therefrom, into the natural glenoid 314. The pegs can be used to resist various motions of the glenoid implant, such as rotation, translation and the like. Further, the pegs allow for cementation points to cement the glenoid implant to the natural glenoid 314, if selected. Regardless, the glenoid template 81 can be used relative to the natural glenoid 314 to form various bores, openings, and the like in the natural glenoid 314.

Once the various bones of the anatomy have been resected, including the natural glenoid 314 and the natural humerus 310, the various implants can be implanted. The natural humerus 310 may need to be further prepared, such as broaching the IM canal of the natural humerus 310. Therefore, a broach may be provided and used to broach a selected portion of the IM canal of the natural humerus 310. Various sizes of broaches may be used to progressively enlarge the broached area of the natural humerus 310, as is generally known in the art.

After inserting the stems 40, 42 or 44 into the medullary canal using impaction, the humeral head 60 is coupled to the locking taper formed on the stem proximal end 50. Coupling mechanism 52 of the humeral head 60 is aligned within the patient to place the central stem axis 46' with the central stem axis 46 of the stem 40. An impact force is applied to the stem in a direction of the central stem axis 46'. As can be seen in the figures, this axis is substantially not in line with the axis defining the curved articulating surface of the humeral head 60.

Figure 20B:
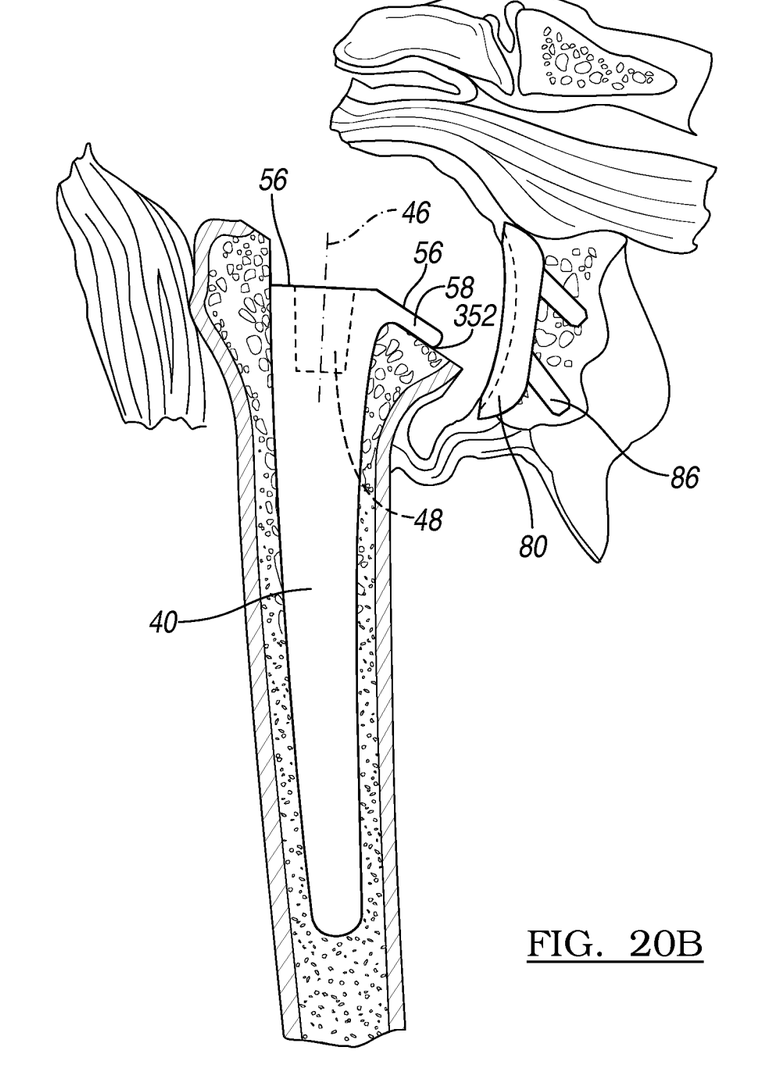
Figure 21:
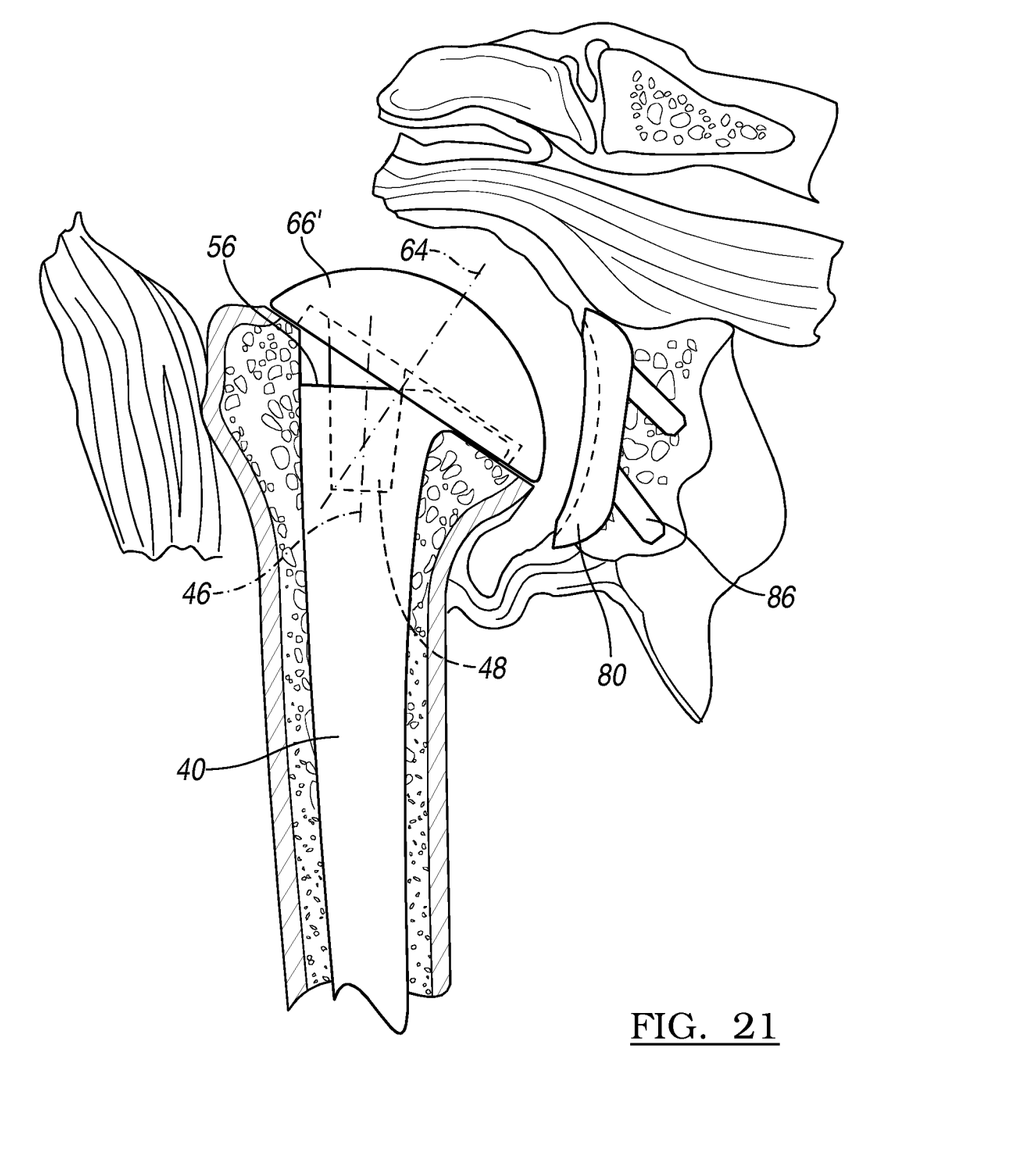
FIG. 21 shows the coupling of the head shown in FIG. 10 to the stem shown in FIG. 2.

FIGS. 20a and 20b represent cross-sectional views of an inserted humeral stem and glenoid prosthetic as shown in FIGS. 4 and 14. It is specifically envisioned that the physician can use a trailing head (66' of FIG. 21) to determine the proper articulation of the shoulder joint. Once the proper head size is determined, the humeral head 60 can be permanently coupled to the stem 42. Once the head is positioned, impact forces are imparted onto the head along the central stem axis 46, coupling the humeral head 60 to the stem 42.

Figure 22:
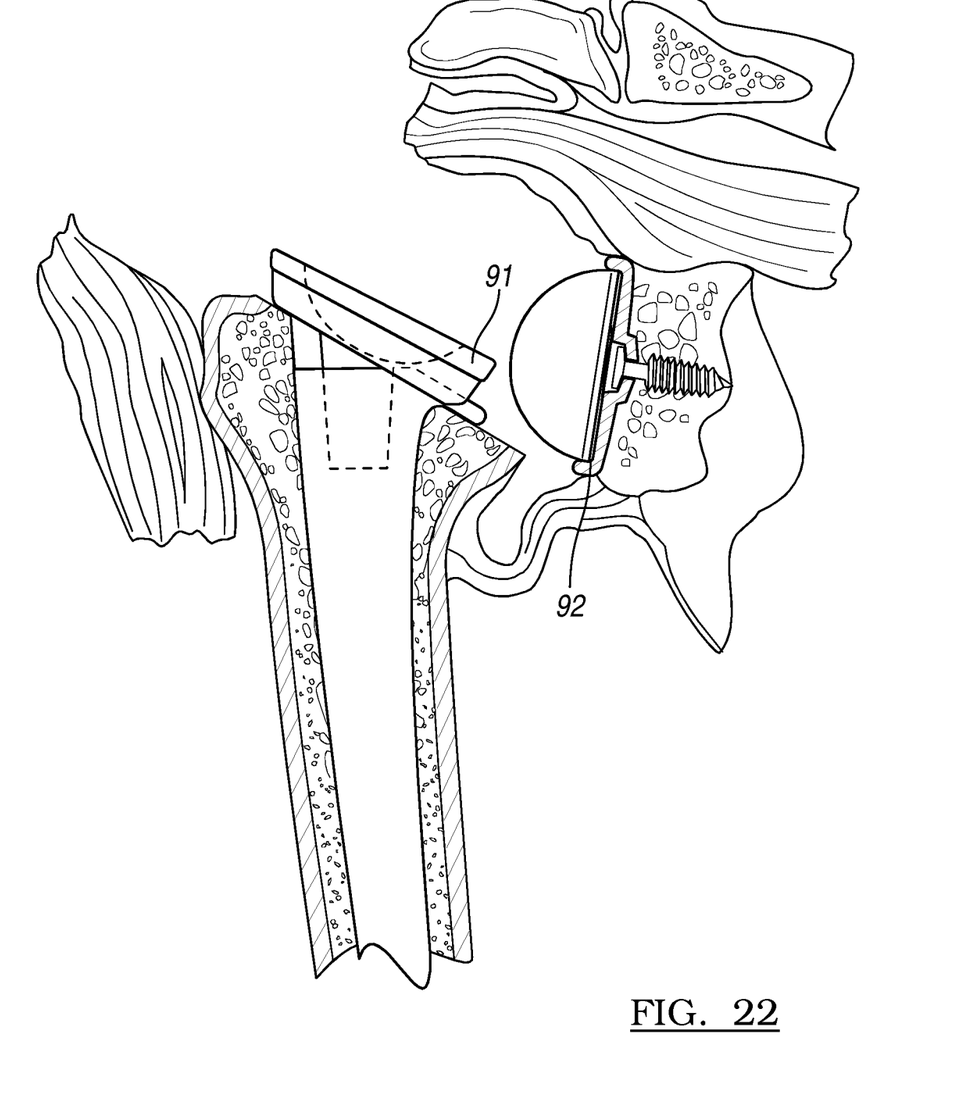
FIG. 22 represents the stem according to FIG. 2 used in a reverse shoulder application.

As shown in FIG. 22, the superior approach can be used to implant a reverse shoulder prosthetic. In this regard, the proximal end of the stem 42 can have a cup member 91 configured to couple to a spherical glenoid implant 92 positioned at a resected glenoid. It is envisioned the cup member 91 can have a fixation member having the central stem axis 46 as previously described'.

Following implantation, the soft tissue balance can again be assessed, and then the split in the rotator interval can be closed. The deltoid can be repaired back to the acromion. Subcutaneous tissues and skin can then be closed per the surgeon's usual routine.

Various portions described herein can be provided in a kit. The kit can include any appropriate portions that can be used in a selected procedure, such as a glenoid and/or humeral procedure and can include a plurality of the broaches, a plurality of the humeral implants, a plurality of humeral heads, a plurality of the glenoid implants, and any other appropriate portion. Therefore, the kit can be used for a plurality of procedures and need not be customized for a particular procedure or patient. Further, the kit can include a plurality of portions that allow it to be used in several procedures for many differing anatomies, sizes, and the like. Further, various other portions, such as the reamer, the glenoid template, or other appropriate portions can be provided for a plurality of different patients.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for performing an arthroplasty on at least one of a glenoid or a humerus of a glenohumeral joint comprising:
   forming an entry incision in soft tissue superior and lateral to the glenohumeral joint;
   forming a passage from the entry incision to the glenohumeral joint;
   inserting a cutting instrument through the passage and cutting a natural humeral head of the humerus to prepare the humerus to receive an implant including a stem while the humeral head has no dislocation at all with respect to the glenoid and remains in its anatomical position;
   inserting the implant through the passage, and securing the implant relative to the humerus with the implant oriented such that a longitudinal axis of the stem extends substantially parallel to a longitudinal axis of the humerus; and
   maintaining both a subscapularis muscle and a supraspinatus muscle associated with the glenohumeral joint intact and completely connected to surrounding bone during an entirety of the arthroplasty.

2. The method of claim 1, further comprising: forming only a single entry incision.

3. The method of claim 1, further comprising: forming the passage through a deltoid muscle substantially superior and lateral of the glenohumeral joint.

4. The method of claim 1, further comprising: inserting through the passage the implant including an articulation surface.

5. The method of claim 1, further comprising: inserting through the passage the implant including an articulation surface, a first axis extending through an axial center of the articulation surface, a planar coupling surface that lies in a plane that is perpendicular to the first axis, and a second axis extending through an axial center of the stem, the second axis is non-orthogonal to the coupling surface.

6. The method of claim 1, wherein securing the implant relative to the humerus further comprises: impacting the implant along a first axis that is generally parallel to a second axis, the second axis is a longitudinal axis of the intramedullary canal of the humerus.

7. The method of claim 1, further comprising:
   inserting a reamer through the entry incision;
   reaming the glenoid with the reamer;
   inserting a glenoid implant through the passage; and
   securing the glenoid implant to the glenoid.

8. A method for performing an arthroplasty on at least one of a glenoid or a humerus of a glenohumeral joint comprising:
   forming an entry incision in soft tissue superior and lateral to the glenohumeral joint;
   forming a passage from the entry incision to the glenohumeral joint through a deltoid muscle substantially superior and lateral of the glenohumeral joint;
   inserting a cutting instrument through the passage and cutting a natural humeral head of the humerus while the humeral head is in cooperation with a glenoid, has no dislocation at all with respect to the glenoid, and remains in its anatomical position to prepare the humerus to receive an implant;
   inserting through the passage the implant including an articulation surface with a first axis extending through an axial center of the articulation surface, a planar coupling surface that extends in a plane orthogonal to the first axis, and a stem with a second axis extending through an axial center of the stem and substantially parallel to a longitudinal axis of the stem, the second axis is non-orthogonal to the coupling surface and is substantially parallel to a longitudinal axis of the humerus;
   orienting the implant such that the second axis is substantially parallel to a longitudinal axis of an intramedullary canal of the humerus;
   securing the implant relative to the humerus; and
   maintaining both a subscapularis muscle and a supraspinatus muscle intact during an entirety of the arthroplasty procedure.

9. The method of claim 8, further comprising: forming only a single entry incision.

10. The method of claim 9, further comprising: forming the passage to extend from the single entry incision to the glenohumeral joint generally interiorly and toward a sagittal plane of a patient.

11. The method of claim 8, further comprising: resecting a portion of the humeral head while the humeral head is in cooperation with the glenoid.

12. The method of claim 8, further comprising: inserting through the passage the implant, the stem of the implant including a first coupling member that is offset from a second coupling member.

13. The method of claim 8, further comprising: inserting through the passage the implant, the stem of the implant is modular.

14. A method for performing an arthroplasty on at least one of a glenoid or a humerus of a glenohumeral joint comprising:
   forming an entry incision in soft tissue superior and lateral to the glenohumeral joint;
   forming a passage from the entry incision to the glenohumeral joint through a deltoid muscle substantially superior and lateral of the glenohumeral joint;
   inserting a cutting instrument through the passage and cutting a humeral head of the humerus while the humeral head is in cooperation and undislocated with a glenoid to prepare the humeral head to receive an implant including an articulation surface and a stem;
   resecting at least a portion of the humeral head while the humeral head is in cooperation with the glenoid;

inserting the implant through the passage, and securing the implant relative to the humerus with the implant oriented such that the stem is confined to an area superior to an intramedullary canal of the humerus and a longitudinal axis of the stem extends substantially parallel to a longitudinal axis of the humerus; and maintaining a subscapularis muscle and a supraspinatus muscle proximate to the glenohumeral joint intact and completely connected to surrounding bone during the entire arthroplasty procedure.

15. The method of claim 14, further comprising: forming only a single entry incision during the entire arthroplasty procedure.

16. The method of claim 14, further comprising:

performing the entire arthroplasty without resecting and without incising the subscapularis muscle and ligaments associated with the subscapularis muscle; and performing the entire arthroplasty without resecting and without incising the supraspinatus muscle and ligaments associated with the supraspinatus muscle.

17. The method of claim 14, wherein securing the implant relative to the humerus further comprises: impacting the implant along an axis that is generally parallel to a longitudinal axis of the humerus.

\* \* \* \* \*